United States Patent [19]

Kanda

[11] Patent Number: 5,088,822
[45] Date of Patent: Feb. 18, 1992

[54] MEAT FRESHNESS MEASURING APPARATUS

[75] Inventor: Masahiko Kanda, Osaka, Japan

[73] Assignee: Sumitomo Electric Industries, Ltd., Osaka, Japan

[21] Appl. No.: 580,104

[22] Filed: Sep. 7, 1990

[30] Foreign Application Priority Data

Sep. 8, 1989 [JP] Japan ................................ 1-234386

[51] Int. Cl.$^5$ ........................... G01J 3/42; G01J 3/50
[52] U.S. Cl. ..................................... 356/326; 356/407
[58] Field of Search ............... 356/320, 326, 328, 402, 356/407

[56] References Cited

FOREIGN PATENT DOCUMENTS

| 0221642 | 5/1987 | European Pat. Off. ............ 356/407 |
| 59-107256 | 6/1984 | Japan . |
| 59-130200 | 7/1984 | Japan . |
| 59-232097 | 12/1984 | Japan . |
| 1-156664 | 6/1989 | Japan . |

OTHER PUBLICATIONS

Watanabe et al.; pp. 233-248.
Bulletin of thee Japanese Society of Scientific Fisheries, vol. 36, No. 2, 1970, p. 177; "Significance in Measuring Volatile Base and Trimethylamine Nitrogen and Nucleotides in Fish Muscle . . . " by Uchiyama et al. (4/8/91).
Bulletin of the Japanese Society of Scientific Fisheries, vol. 36, No. 9, 1970, p. 977, "The Current Studies on the Freshness of Fish with Special Reference to Nucleid Acids and their Related Compounds" by Uchiyama et al., 4/8/91.
Bulletin of the Japanese Society of Scientific Fisheries, vol. 24, No. 9, 1959, pp. 749 & 750 "A New Method for Estimating the Freshness of Fish" by Saito et al.
Kato et al., pp. 1039-1044.

Primary Examiner—F. L. Evans
Attorney, Agent, or Firm—W. G. Fasse; D. H. Kane, Jr.

[57] ABSTRACT

A meat freshness measuring apparatus measures the freshness of meat by detecting changes in a pigment contained in the meat. For this purpose, the meat (2) is exposed to rays of light of different wavelengths applied from a light source (1), and the rays obtained from the meat are separated into spectra for the respective wavelengths, which are received by a photoelectric conversion element (4). Spectrum data for each wavelength are amplified and then the amplified data are converted to a digital signal by an A/D converter (7), whereby the digital signal is stored in a RAM (12). Based on the stored spectrum data and using a prescribed equation of calculation, a content of the pigment in the meat is calculated and outputted by a CPU (10).

3 Claims, 5 Drawing Sheets

| | | | | | |
|---|---|---|---|---|---|
| R1 | E11 E12 E13 | | E1m | —12a1 | ⎫ |
| R2 | E21 E22 E23 | | E2m | —12a2 | ⎪ |
| | | | | | ⎬ SPECTRUM DATA |
| Rk | Ek1 Ek2 | | Ekm | —12ak | ⎪ |
| | | | | | ⎪ |
| Rn | En1 En2 | | Enm | —12an | ⎭ |
| R̄ | Ē1 Ē2 | | Ēm | —12b | AVERAGE SPECTRUM |
| | TOTAL Mb CONTENT | | | —12c1 | |
| | Mb% | | | —12c2 | |
| | MbO% | | | —12c3 | |
| | MM% | | | —12c4 | |
| | | | | | |
| C | C1 C2 | | Cm | —12d | CALIBRATION DATA |
| A | A1 A2 | | Am | —12e | ABSORPTION SPECTRUM DATA |

FIG.7

LIGHT QUANTITY / WAVELENGTH

MEAT FRESHNESS MEASURING APPARATUS

FIELD OF THE INVENTION

The present invention relates generally to a meat freshness measuring apparatus. More particularly, the present invention relates to a meat freshness measuring apparatus for exposing meat to light from a light source and for analyzing a specific pigment component representing freshness in the meat based on light reflected or transmitted from the meat.

BACKGROUND INFORMATION

Freshness of beef or other meat is an important factor in quality control in a meat distribution process, or in a meat supply business. There have been proposed various methods or apparatus for measuring the freshness of meat. One of such apparatus is a meat freshness measuring apparatus described in Japanese Patent Laying-Open No. 1-156664. According to this Japanese Patent Document, it was made clear by studies of Saito et al (Transactions of the Japanese Society of Scientific Fisheries, Vol. 24, pp. 749–750: 1957) and Uchiyama, Ehira et al (Transactions of the Japanese Society of Scientific Fisheries, Vol. 36, pp. 177–187, 977–992: 1970) that a composition ratio of nucleic acid compounds contained in beef or other animal meat has a close relation with freshness. More specifically, since ATP (adenosine triphosphate) in beef or other animal meat decomposes, after the death, in the order of ATP→ADP (adenosine triphosphate)→AMP (adenosine monophosphate)→IMP (inosinic acid)→Hx R (inosine)→Hx (buxanthine), the following K value is used as an index of freshness.

K value
$(\%) = (H \times R + Hx)/(ATP + ADP + AMP + IMP + H \times R + Hx) \times 100.$ In addition, it was found as a result of the study by Watanabe et al (Papers on Polymers, Vol. 41, pp. 233–248: 1984) that ATP and ADP decompose rapidly after death, and that there is a very small quantity of AMP. Thus, it was found that there is no practical problem if the terms of ATP, ADP and AMP are omitted from the above-mentioned expression K value.

The K value has been conventionally measured by various methods such as a column chromatographic method (Kato et al, Transactions of the Japanese Society of Scientific Fisheries, Vol. 39, pp. 1039–1044: 1973), an oxygen method (Uda et al, Japanese Patent Publication No. 59-130200), and a sensor method (Watanabe et al, Japanese Patent Publication No. 59-107256, or Arai et al, Japanese Patent Publication No. 59-232097).

Another method conventionally used is a spectral method utilizing reflected or transmitted light, in which conditions of a meat pigment can be directly detected. Thus, this method is useful for determining what influence the handling and processing of meat exert on the stability of the meat pigment. For this method an application of a laser beam may be considered. However, measuring apparatus using this method are suited for use in laboratories but not suited for practical use in meat processing factories.

SUMMARY OF THE INVENTION

Therefore, the principal object of the present invention is to provide a meat freshness measuring apparatus capable of measuring freshness of meat by spectral analysis based on changes of a pigment (such as myoglobin) in the meat in real time utilizing reflected or transmitted light from the meat.

Briefly stated, in the apparatus of the present invention, meat is exposed to rays of different wavelengths and the rays of the respective wavelengths from the meat are separated into spectra of the respective wavelengths. The rays of the spectra of the respective wavelengths are received and spectrum data is stored for each wavelength. Based on the spectrum data for each wavelength thus stored and a prescribed calculation equation, a content of a pigment in the meat is calculated and outputted.

Consequently, according to the present invention, the contents of pigments in meat are calculated according to spectrum data for each wavelength obtained from the meat. Thus, the apparatus can be compact and light, which makes it possible to measure the freshness of meat efficiently and in a handy manner in various places as required.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 8 to 10 are flow charts for explaining specific operations of the embodiment of the invention. Particularly, FIG. 8 represents a main routine; FIG. 9 represents a calibration subroutine; and FIG. 10 represents a spectrum measurement subroutine.

DESCRIPTION OF THE PREFERRED EMBODIMENTS

Figure 2:
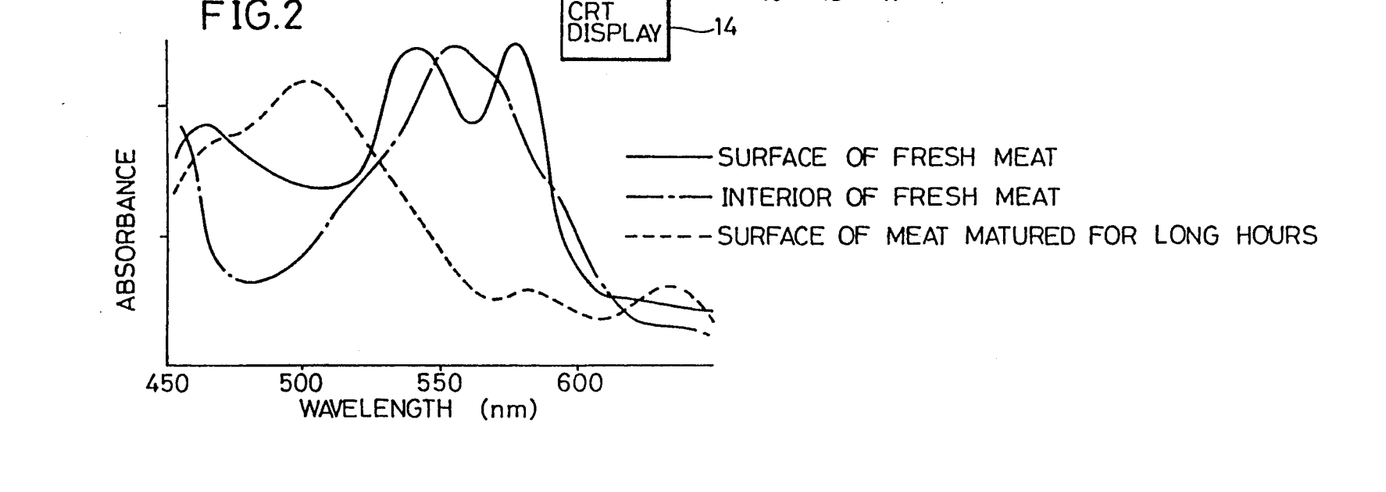
FIG. 2 is a graph showing spectra in specimens of refrigerated meat blocks in three different conditions.
Figure 3:
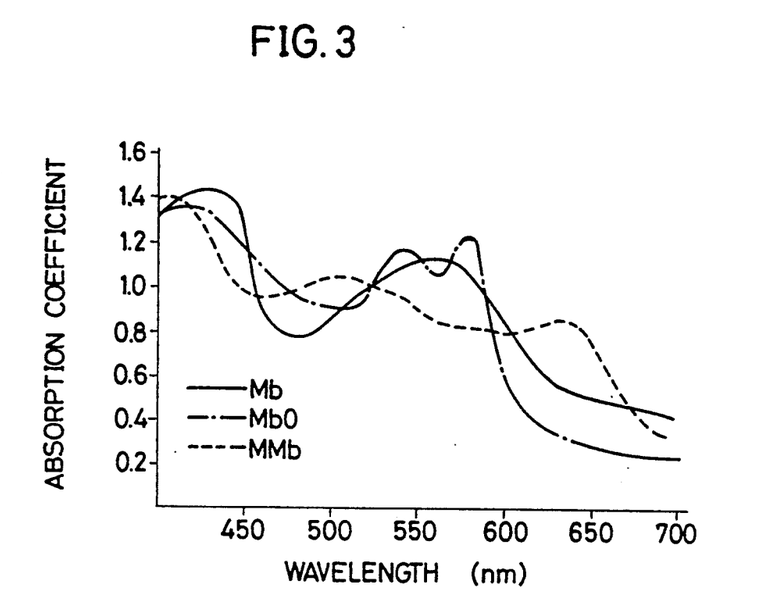
FIG. 3 is a graph showing absorption spectra of Mb, MbO and MMb.
Figure 4:
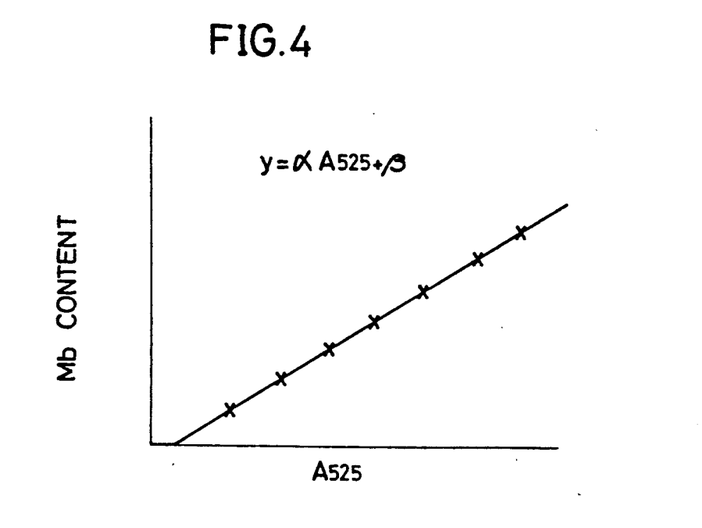
FIG. 4 is a graph showing a calibration curve of an absorbance $A_{525}$ of a wavelength 525 nm and a content of Mb.

Referring first to FIGS. 2, 3 and 4, the general principles on which the present invention is based will now be described. A surface of a carcass refrigerated one night after slaughter presents a color inherent in oxymyoglobin (hereinafter referred to as MbO). An internal portion thereof cut by a knife presents a color inherent in myoglobin (hereinafter referred to as Mb). A surface of a carcass stocked for a very long period presents a color of metmyoglobin (hereinafter referred to as MMb). According to the present invention, freshness of meat is measured by analyzing spectral changes of Mb, MbO and MMb. FIG. 3 shows absorption spectra of Mb, MbO and MMb with absorption coefficients thereof being set in equal ranges. In this figure, 525 nm represents an isosbestic point of Mb, MbO and MMb. Therefore, the absorbance $A_{525}$ of a wavelength 525 nm is as follows.

$$A_{525} = K_{525}(C^{Mb} + C^{MbO} + C^{MMb}) \cdot D \tag{1}$$

where
$K_{525}$ absorption coefficients of Mb, MbO, MMb at the wavelength 525 nm
$C^{Mb}$: concentration of Mb (myoglabin)
$C^{MbO}$: concentration of MbO (oxymyoglobin)
$C^{MMb}$: concentration of MMb (metmyozlabin)
D: optical path at the time of reflection spectrum measurement.

First, $C^{Mb}$ will be obtained. A wavelength 474 nm is an isosbestic point of MbO and MMb, and absorbance $A_{474}$ thereof is as follows.

$$A_{474} = K^{Mb}{}_{474} \cdot C^{Mb} \cdot D + K_{474} \cdot (C^{Mbo} + C^{MMb}) \cdot D \tag{2}$$

From the equations (1) and (2), the following equation is obtained.

$$K_{474} \cdot (A_{525}/D) - K_{525}$$
$$(A_{474}/D) = K_{525} \cdot K_{474} \cdot C^{Mb} - K^{Mb}{}_{474} \cdot K_{525} \cdot C^{Mb}$$

Therefore, $C^{Mb}$ is obtained by the following equation.

$$C^{Mb} = (K_{474} \cdot A_{525} - K_{525} \cdot A_{474}) / [(K_{525} \cdot K_{474} - K^{Mb}{}_{474} \cdot K_{525}) \cdot D] \tag{3}$$

Next, as for MbO, a wavelength 614 nm represents an isosbestic point of Mb and MMb, and accordingly absorbance $A_{614}$ thereof is as follows.

$$A_{614} = K^{Mb}{}_{614} \cdot C^{MbO} \cdot D + K_{614}(C^{Mb} + C^{MMb}) \cdot D \tag{4}$$

Therefore, in the same manner as in the case of Mb, from the equations (1) and (4), $C^{MbO}$ is obtained by the following equation.

$$C^{MbO} = (K_{614} \cdot A_{525} - K_{525} \cdot A_{614}) / [(K_{525} \cdot K_{614} - K^{MbO}{}_{614} \cdot K_{525}) \cdot D] \tag{5}$$

As for MMb, a wavelength 572 nm represents an isosbestic point of Mb and MbO and thus, in the same manner, $C^{MMb}$ is obtained by the following equation.

$$C^{MMb} = (K_{572} \cdot A_{525} - K_{525} \cdot A_{572}) / [(K_{525} \cdot K_{572} - K^{MMb}{}_{572} \cdot K_{525}) \cdot D] \tag{6}$$

The above-mentioned wavelengths may be within certain ranges. For instance, the wavelength 474 nm for Mb may be 370 nm or 597 nm; the wavelength 614 nm for MbO may be 675 nm or 460 nm; and the wavelength 572 nm for MMb may be 460 nm, 507 nm, 555 nm or 597 nm.

In addition, from the equation (1), the following equation is obtained.

$$C^{Mb} + C^{MbO} + C^{MMb} = A_{525} / K_{525} \cdot D \tag{7}$$

If a calibration curve of $A_{525}$ and the Mb content is prepared as shown in FIG. 4, the following equation (8) is obtained.

$$\text{Total Mb content} = \alpha \cdot A_{525} + \beta \tag{8}$$

A percentage of Mb is, from the equations (3) and (7), as follows.

$$\begin{aligned}
Mb \% &= C^{Mb} \times 100/(C^{Mb} + C^{MbO} + C^{MMb}) \\
&= (K_{525}/A_{525}) \cdot (K_{474} \cdot A_{525} - K_{525} \cdot A_{474})/(K_{525} \cdot K_{474} - K^{Mb}{}_{474} \cdot K_{525}) \times 100 \\
&= (1 - K_{525}/K^{Mb}{}_{474} \cdot A_{474}/A_{525}) \times 100
\end{aligned} \tag{9}$$

In the same manner, percentages of MbO and MMb are obtained as follows.

$$MbO\% = (1 - K_{525}/K^{Mbo}{}_{614} \cdot A_{614}/A_{525}) \times 100 \tag{10}$$

$$MMb\% = (1 - K_{525}/K^{MMb}{}_{572} \cdot A_{572}/A_{525}) \times 100 \tag{11}$$

According to the present invention, Mb%, MbO%, MMb% are measured on the basis of the above mentioned principles. In the following, a more detailed description will be made in connection with an embodiment.

The foregoing terms are defined as follows:
$A_{525}$: absorbance of light at a wavelength 525 nm;
$K_{525}$: respective absorption coefficients of Mb, MbO, MMb at the wavelength 525 nm;
D: length of optical path at the time of reflection spectrum measurement;
Mb%: percentage of Mb content $$\frac{C^{Mb}}{C^{Mb} + C^{MbO} + C^{MMb}} \times 100$$

$K^{Mb}$: absorption coefficient of Mb at a wavelength 474 nm;
$A_{474}$: absorbance of light at the wavelength 474 nm;
MbO%: percentage of MbO content $$\frac{C^{MbO}}{C^{Mb} + C^{MbO} + C^{MMb}} \times 100$$

$K^{MbO}{}_{614}$: absorption coefficient of MbO at a wavelength 614 nm;
$A_{614}$: absorbance of light at the wavelength 614 nm;
MMb%: percentage of MMb content $$\frac{C^{MMb}}{C^{Mb} + C^{MbO} + C^{MMb}} \times 100$$

$K^{MMb}{}_{572}$: absorption coefficient of MMb at a wavelength 472 nm; and
$A_{572}$: absorbance of light at the wavelength 572 nm.

Figure 1:
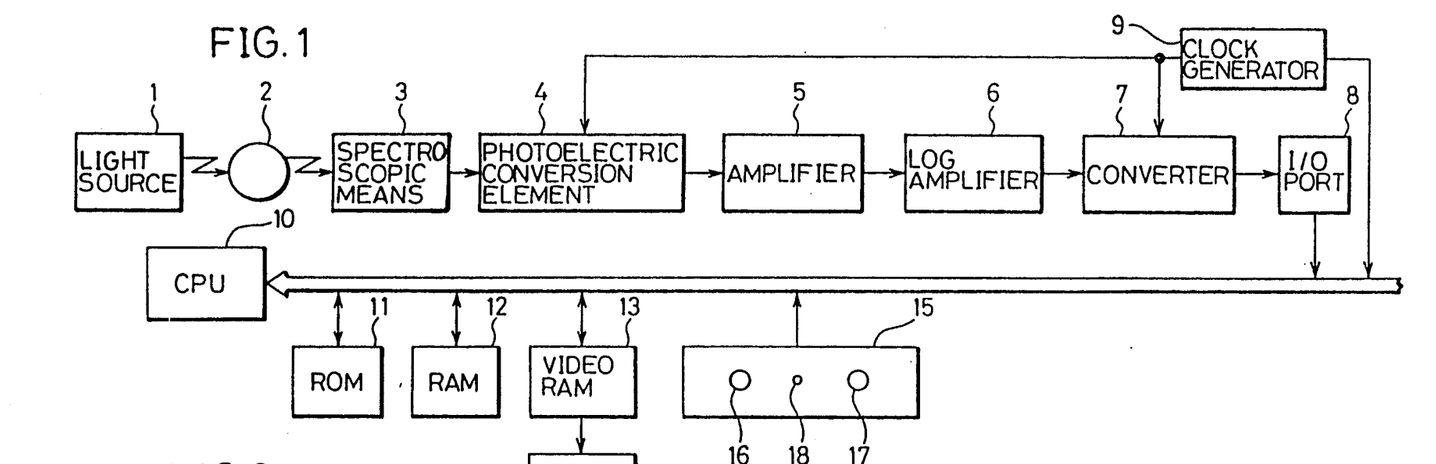
FIG. 1 is a schematic block diagram of an embodiment of the present invention.

FIG. 1 is a schematic block diagram of an embodiment of the present invention. A light source 1 irradiates an object 2 to be measured such as meat. Reflected or transmitted light from the object 2 enters spectroscopic means 3, where it is spectrally separated. A beam of a prescribed wavelength thus obtained is supplied to a photoelectric conversion element 4, where it is converted to an electric signal. The electric signal is amplified by an amplifier 5 and the amplified signal is supplied to a log amplifier 6, where it is converted to a light quantity signal. The light quantity signal is supplied to an A/D converter 7, where it is converted to a digital signal. The digital signal thus obtained is supplied as light quantity data of the prescribed wavelength to a CPU 10 through an I/O port 8 and an I/O bus.

Figure 7:
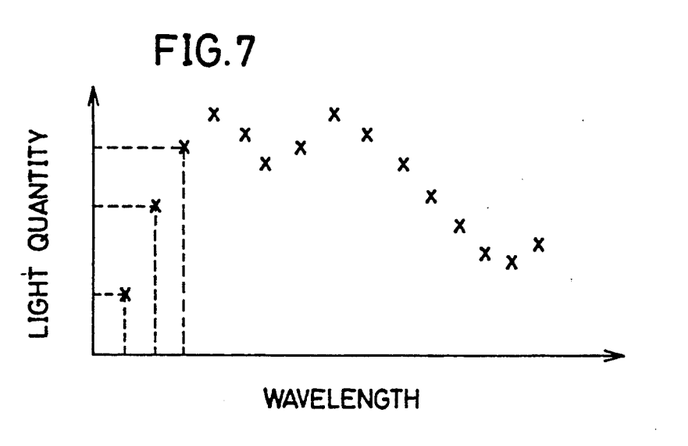
FIG. 7 is a diagram showing an example of spectrum data measured according to the embodiment of the invention.
Figure 8:
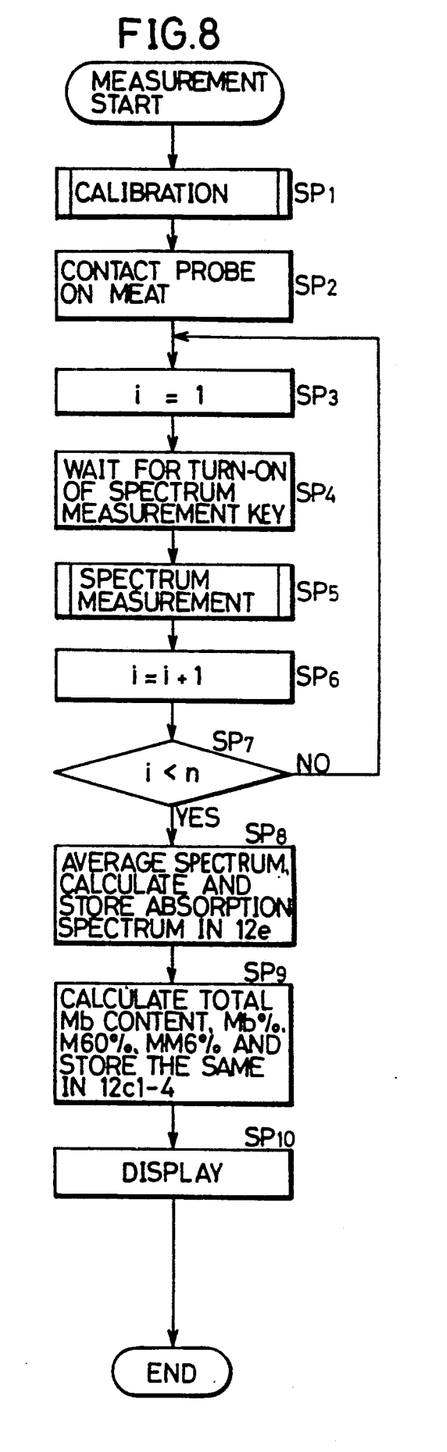
Figure 9:
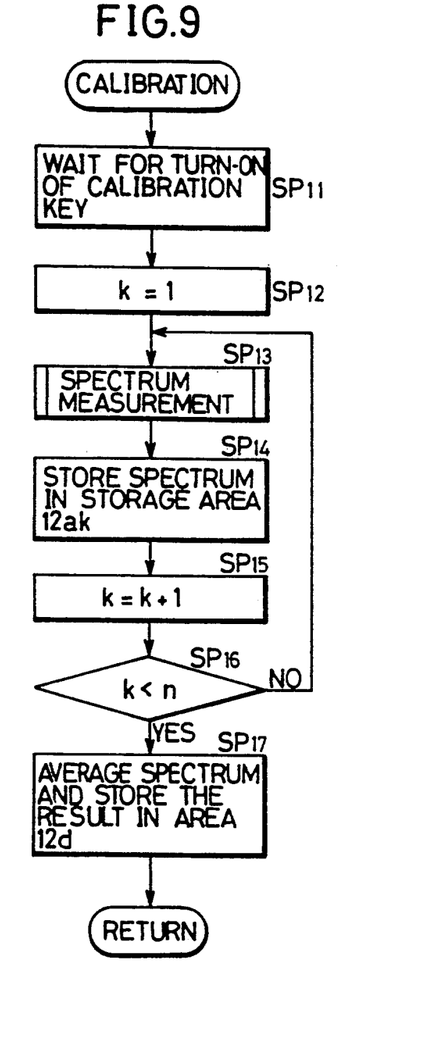

The CPU 10 is connected with a ROM 11, a RAM 12, a video RAM 13, and an operation unit 15 through the I/O bus. Necessary programs for processing by the CPU 10 are stored in the ROM 11. These are based for example, on the below-described flow charts as shown in FIGS. 7 to 9. The RAM 12 stores various data necessary for processing by the CPU 10 as will be described in detail below with reference to FIG. 5. The video RAM 13 temporarily stores data processed by the CPU 10 and displays the data on a CRT display 14.

Figure 10:
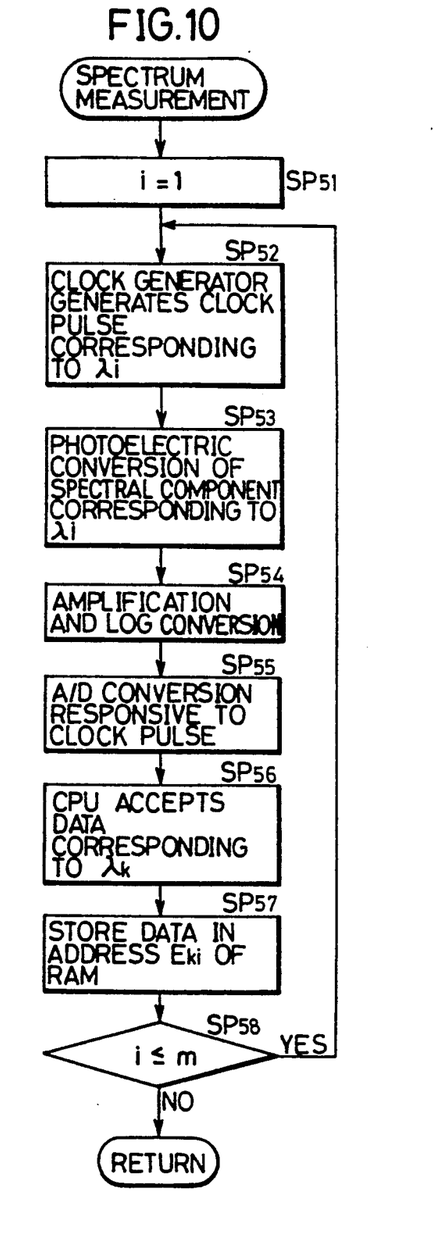

The operation unit 15 includes a calibration key 16, a spectrum measurement key 17 and an analysis prohibition indicator 18. The calibration key 16 is provided to give an instruction for obtaining a reference spectrum at the time of obtaining an absorption spectrum. The spectrum measurement key 17 is provided to initiate the measurement of spectrum data. The analysis prohibition indicator 18 indicates that sampling data cannot be analyzed. The calibration key 16 and the spectrum measurement key 17 can individually provide instructions to the CPU 10. By operating those keys, an operation as described below based on the flow charts shown in FIGS. 9 and 10 is executed.

A clock generator 9 supplies clock pulses to the photoelectric conversion element 4, the A/D converter 7 and the I/O bus.

Figure 5:
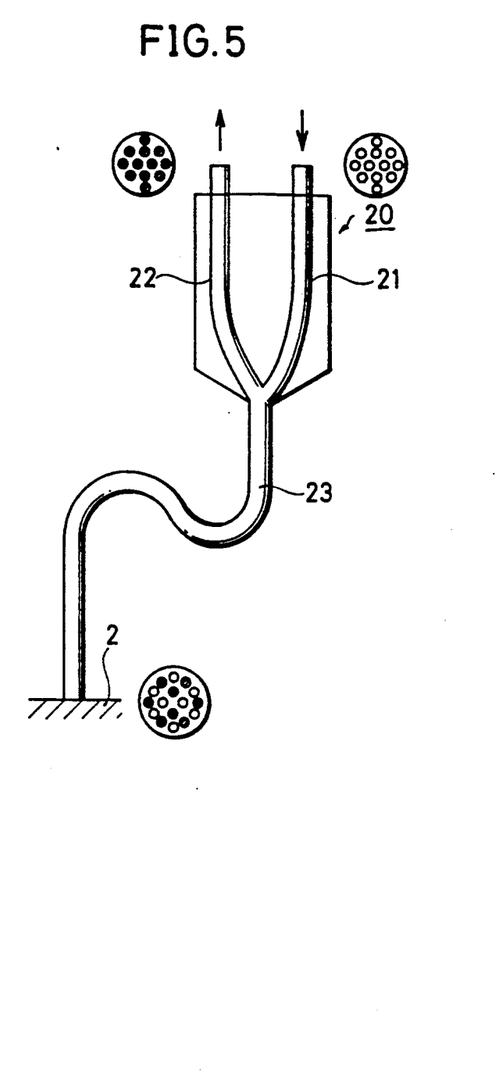
FIG. 5 is a view showing a fiber probe.

FIG. 5 shows a fiber probe 20 for transmitting light from the light source 1 to the object 2 to be measured and for transmitting the light reflected from the object 2 to the spectroscopic means 3. The fiber probe 2 includes a light transmitting fiber bundle 21 and a light receiving fiber bundle 22, which are joined together in an intermediate portion to form a fiber bundle 23. An end of the light transmitting fiber bundle 21 receives the light from the light source 1. An end of the fiber bundle 23 on the other side contacts the object 2. The light transmitted through the light transmitting fiber bundle 21 is reflected by the object 2 and is communicated to the spectroscopic means 3 through the light receiving fiber bundle 22. If the probe is of a transmission type, the transmitted light may be communicated to the spectroscopic means 3 through the light receiving bundle 22 without integrally forming the light transmitting fiber bundle 21 and the light receiving fiber bundle 22.

Figure 6:
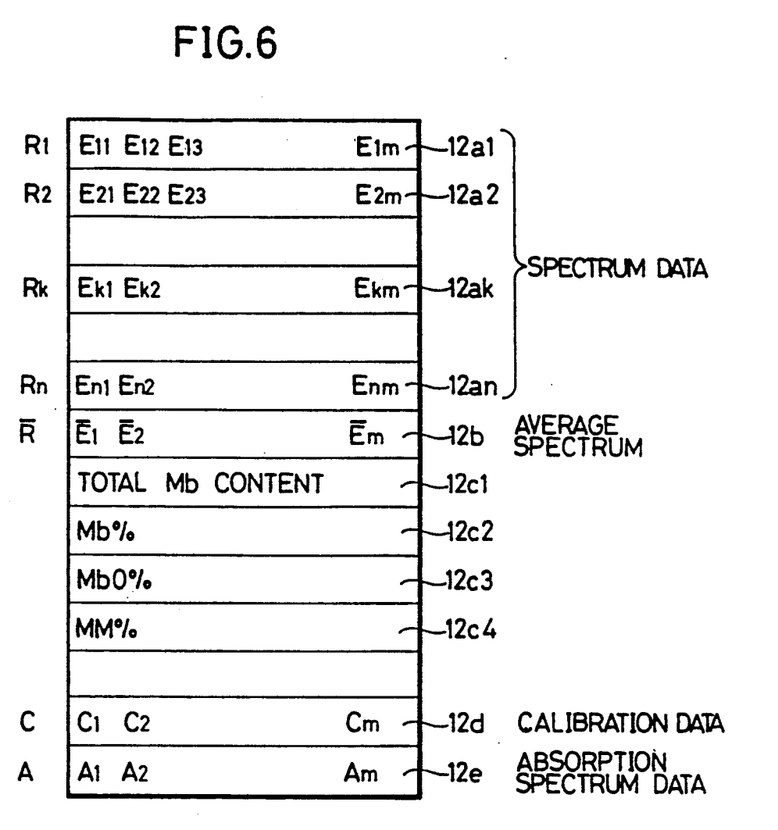
FIG. 6 is a diagram showing data stored in the RAM shown in FIG. 1.

FIG. 6 is a diagram showing data stored in the RAM 12 shown in FIG. 1, and FIG. 7 is a graph showing an example of spectrum data measured in the embodiment of the present invention.

In the above-described measurement apparatus shown in FIG. 1, the light from the light source 1 is applied to the object 2 through the light transmitting fiber bundle 21 of the fiber probe 20 shown in FIG. 5 and the reflected or transmitted light therefrom is directed to the spectroscopic means 3 through the light receiving fiber bundle 22, by which a spectrum is produced, and then it is converted to an electric signal by the photoelectric conversion element 4. The electric signal is amplified by the amplifier 5 and the amplified signal is converted to a light quantity signal by the log amplifier 6, whereby the light quality signal is sampled by the A/D converter 7. Then, results $E_{11}$, $E_{12}$, $E_{13}$, ..., $E_{1m}$ of the sampling with respective wavelengths $\lambda_1$, $\lambda_2$, $\lambda_3$, ... $\lambda_m$ are stored as spectrum data in an area $12a1$ of the RAM 12 shown in FIG. 6. Distribution of those spectrum data is as shown in FIG. 7.

Referring to FIG. 6, the data stored in the RAM 12 will be described. The RAM 12 includes areas $12a1$, $12a2$ ... $12ak$ ... $12an$, $12b$, $12c1$ to $12c4$, $12d$ and $12e$. Spectrum data the number of which is n are stored in the areas $12a1$ to $12an$. Average spectrum matrix data $\overline{E}_1$, $\overline{E}_2$ ... $\overline{E}_m$ are stored in the area $12b$. The total Mb content, respective percentages of Mb%, MbO%, MMb% analyzed by absorption spectra are stored in the areas $12c1$ to $12c4$. Measured calibration data is stored in the area $12d$, and absorption spectrum data are stored in the area $12e$.

FIGS. 8 to 10 are flow charts for explaining a specific operation of the embodiment of the present invention. Particularly, FIG. 8 represents a main routine; FIG. 9 represents a calibration subroutine; and FIG. 10 represents a spectrum measurement subroutine. Referring to FIGS. 1 to 10, the specific operation of the embodiment will be described. First, in the main routine shown in FIG. 8, when measurement is started, the program proceeds to a calibration mode in step SP1, in which the calibration subroutine shown in FIG. 9 is executed. In the calibration mode, the top end of the fiber probe 20 shown in FIG. 5 is in contact with a material such as a reference white plate having a fixed reflectance with respect to a measured wavelength range instead of the object 2 to be measured. In the case of a probe of a transmission type, light from the light transmitting fiber bundle 21 may be directly applied to the light receiving fiber bundle 22.

The CPU 10 waits for the turn-on of the calibration key 16 in step SP11 shown in FIG. 9 and when it is determined that the calibration key 16 is on, the CPU 10 sets the number k of measurements to 1 in step SP12. Then, the CPU 10 executes the spectrum measurement subroutine in step SP13. In the spectrum measurement subroutine, the number i of measurements is set to 1 in step SP51 as shown in FIG. 10 so as to sample the first light quantity. In step SP52, a clock pulse corresponding to the wavelength $\lambda_1$ is generated from the clock generator 9. When this clock pulse is generated from the clock generator 9, the photoelectric conversion element 4 photoelectrically converts a spectral component corresponding to the wavelength $\lambda_1$ provided by the spectroscopic means 3 in step SP53.

In step SP54, the amplifier 5 amplifies an output of the photoelectric conversion element 4 and the log amplifier 6 converts the output of the amplifier 5 to a light quantity signal. In step SP55, the A/D converter 7 converts the light quantity signal to a digital signal in response to the clock pulse supplied from the clock generator 9. The digital signal obtained by the A/D converter 7 is supplied to the CPU 10 from the I/O port 8 through the I/O bus. The CPU 10 accepts digital data $E_{k1}$ corresponding to the wavelength $\lambda_1$ in step SP56, and stores the data $E_{k1}$ in the area $12ak$ of the the RAM 12 in step SP57. The CPU 10 determines in step SP58 whether the number i is smaller than m. If it is determined that the number i is smaller than m, the CPU 10 returns to step SP52.

In step SP52, a clock pulse corresponding to the wavelength $\lambda_2$ is generated from the clock generator 9. Subsequently, in the same manner as described above, the operation in steps SP53 to SP57 is executed, whereby the sampling data $E_{k2}$ of the wavelength $\lambda_2$ is stored in the area $12ak$ of the RAM 12. The CPU 10 repeats this operation, whereby the spectrum data $E_{k1}$, $E_{k2}$ ... $E_{km}$ having m wavelength components are stored in the storage area $12ak$. Then, the CPU 10 returns to the calibration subroutine shown in FIG. 9.

The CPU 10 stores, in step SP15, the spectrum data stored in the area $12ak$ into the area $12a1$. Thus, if the initial condition set in step SP12 is k=1, the measured spectrum data is stored in the area 12a1, and subsequently, each time the number k is set to 2, 3, ..., n, the spectrum data is stored successively in the areas 12a2, 12a3, ..., 12an.

In step SP15, the initial condition is set to k=k+1 and, in step SP16, it is determined whether k is smaller than n. If k is smaller than n, the CPU 10 returns to the above-mentioned step SP13. Thus, sampling for the spectral output from the object 2 is repeated m times in steps SP13 to SP16. In step SP17, the sampled spectrum data are averaged and the result is stored as calibration data in the area 12d. After that, the CPU 10 returns to step SP2 shown in FIG. 8.

In step SP2, the top end of the fiber probe 20 shown in FIG. 5 is brought into contact with a specimen of meat as the object 2 to be measured. In step SP3, the CPU 10 sets the number i of measurements to 1, and the CPU 10 waits in step SP4 until the spectrum measurement key 17 is operated. When the spectrum measurement key 17 is operated, the CPU 10 executes the spectrum measurement subroutine in step SP5. In the spectrum measurement subroutine, steps SP51 to SP58 shown in FIG. 10 are executed in the same manner as described above. Through this spectrum measurement subroutine, the spectrum data of the respective wavelengths are measured, and the number i+1 is set in step SP6. In step SP7, it is determined whether the number i of measurements is smaller than n, and if the number i is smaller than n, the CPU 10 returns to step SP3. Thus, steps SP3 to SP7 are repeated and the spectrum data for the respective wavelengths are measured n times.

In step SP8, the measured spectrum data are averaged and subtraction is performed as to the calibration data $C_1$ to $C_m$ stored in the area 12d. Thus, the following equation:

$$A_i = C_i - \sum_{k=1}^{n} E_{Ki}/n$$

is performed, whereby the absorption spectrum data is stored in the area 12e. After that, the CPU 10 executes calculations of the above-mentioned equations (8), (9), (10) and (11), so as to obtain the entire Mb content, respective percentages of Mb%, MbO%, MMb% and to store those data in the areas 12c1 to 12c4. The CPU 10 displays the entire Mb content, Mb%, MbO%, MMb% stored in the areas 12c1 to 12c4 in step SP9, on the CRT display 14 through the video RAM 13.

As described in the foregoing, according to the embodiment of the invention, meat to be tested is exposed to rays of different wavelengths and the rays of the respective different wavelengths obtained from the meat are received for spectrum analysis. Thus, data representing a pigment of the meat is calculated according to the spectrum pattern and prescribed calculation equations and the data is provided as output. The components of the present apparatus are small so that the apparatus may be compact and light weight, and the freshness of meat can be measured efficiently and in a handy manner in various places.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A meat freshness measuring apparatus for measuring meat freshness by detecting changes in a pigment contained in the meat, comprising: light source means (1) for applying rays of light of different wavelengths to said meat; spectroscopic means (3) for spectrally separating the rays applied to said meat by said light source means and reflected or transmitted from said meat into spectra for the respective wavelengths; light receiving means (4) for receiving the rays of the respective wavelengths separated by said spectroscopic means; storage means (12) for storing spectrum data for each of the wavelengths received by said light receiving means; calculating means for calculating a content of the pigment in said meat according to the spectrum data for each of the wavelengths stored in said storage means and a prescribed equation of calculation; output means (14) for providing the content of the pigment in said meat calculated by said calculating means, calibration mode selecting means (16) for selecting a calibration mode, said calculating means including means (SP11 to SP14) responsive to the selection of the calibration mode by said calibration mode selecting means, for detecting a plurality of spectrum data as a reference for each wavelength, for averaging the data for each wavelength, and for storing the averaged data as calibratrion data, measurement mode selecting means (17) for selecting a measurement mode, and wherein said calculating means include means (SP9) responsive to the selection of the measurement mode by said measurement mode selecting means, for detecting a plurality of spectrum data for each wavelength provided from said light receiving means, averaging the spectrum data and subtracting said averaged data from said calibration data, and calculating a content of the pigment in said meat according to said equation of calculation.

2. The meat freshness measuring apparatus in accordance with claim 1, wherein said calculation means includes means (SP9) for calculating contents of myoglobin (Mb), oxymyoglobin (MbO), and metmyoglobin (MMb) as the content of said pigment.

3. The meat freshness apparatus in accordance with claim 2, wherein said calculating means calculate the following equations:

$$C^{Mb} + C^{MbO} + C^{MMb} = A_{525}/K_{525} \cdot D$$

$$Mb\% = (1 - K_{525}/K_{474}^{Mb} \cdot A_{474}/A_{525}) \times 100 =$$

$$\frac{C^{Mb}}{C^{Mb} + C^{MbO} + C^{MMb}} \times 100$$

$$MbO\% = (1 - K_{525}/K_{614}^{MbO} \cdot A_{614}/A_{525}) \times 100 =$$

$$\frac{C^{MbO}}{C^{Mb} + C^{MbO} + C^{MMb}} \times 100$$

$$MMb\% = (1 - K_{525}/K_{572}^{MMb} \cdot A_{572}/A_{525}) \times 100 =$$

$$\frac{C^{MMb}}{C^{Mb} + C^{MbO} + C^{MMb}} \times 100$$

wherein
$C^{Mb}$ is the concentration of myoglobin,
$C^{MbO}$ is the concentration of oxymyoglobin, $C^{MMb}$ is the concentration of metmyoglobin, and
wherein $A_{525}$: absorbance of light at a wavelength 525 nm;

$K_{525}$: respective absorption coefficients of Mb, MbO, MMb at the wavelength 525 nm;

D: length of optical path at the time of reflection spectrum measurement;

$L^{Mb}_{474}$: absorption coefficient of Mb at a wavelength 474 nm;

$A_{474}$: absorbance of light at the wavelength 474 nm;

$K^{MbO}_{614}$: absorption coefficient of MbO at a wavelength 614 nm;

$A_{614}$: absorbance of light at the wavelength 614 nm;

$K^{MMb}_{572}$: absorption coefficient of MMb at a wavelength 572 nm; and $A_{572}$: absorbance of light at the wavelength 572 nm.

* * * * *

UNITED STATES PATENT AND TRADEMARK OFFICE
CERTIFICATE OF CORRECTION

PATENT NO. : 5,088,822
DATED : February 18, 1992
INVENTOR(S) : Masahiko Kanda

It is certified that error appears in the above-identified patent and that said Letters Patent is hereby corrected as shown below:

Column 3, line 9, replace "(myoglabin)" by --(myoglobin)--;
column 3, line 11, replace "(metmyozlabin)" by
          --(metmyoglobin)--;
column 4, line 33, replace "$K^{Mb}$:" by --$K^{Mb}_{474}$:--;
column 4, line 51, replace "472 nm" by --572 nm--;
column 8, line 29, replace "calibratrion" by --calibration--;
column 10, line 1, replace "$L^{Mb}_{474}$" by --$K^{Mb}_{474}$--.

Signed and Sealed this

Fourth Day of May, 1993

MICHAEL K. KIRK

*Attest:*

*Attesting Officer*   Acting Commissioner of Patents and Trademarks